(12) United States Patent
Mitsuhashi et al.

(10) Patent No.: US 6,887,697 B2
(45) Date of Patent: May 3, 2005

(54) D-AMINOACYLASE AND GENE ENCODING THE SAME

(75) Inventors: Kazuya Mitsuhashi, Tsukuba (JP); Hiroaki Yamamoto, Tsukuba (JP); Akinobu Matsuyama, Tsukuba (JP); Shinji Tokuyama, Shizuoka (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/750,026

(22) Filed: Dec. 31, 2003

(65) Prior Publication Data

US 2004/0166564 A1 Aug. 26, 2004

Related U.S. Application Data

(62) Division of application No. 09/770,517, filed on Jan. 26, 2001, now Pat. No. 6,780,619.

(30) Foreign Application Priority Data

Jan. 27, 2000 (JP) ........................................ 2000-019080
May 22, 2000 (JP) ........................................ 2000-150578

(51) Int. Cl.$^7$ ............................. C12N 9/78; C12N 9/10; C12N 9/14; C07K 1/00; C07H 21/04
(52) U.S. Cl. ...................... 435/227; 435/183; 435/195; 530/350; 536/23.1; 536/23.2
(58) Field of Search ................................. 435/183, 195, 435/227; 530/350

(56) References Cited

FOREIGN PATENT DOCUMENTS

| EP | 0677585 A1 * | 10/1995 | ........... C12N/15/55 |
| EP | 0896057 A2 | 2/1999 | ........... C12N/9/80 |
| EP | 0976828 A1 | 2/2000 | ........... C12N/15/55 |
| WO | WO 00/23598 | 4/2000 | ........... C12N/15/55 |

OTHER PUBLICATIONS

Grifantini et al. Accession AAR82837. Mar. 13, 1996 (Alignment SEQ ID No.: 2).*
Broun et al. Science. Nov. 13, 1998;282(5392):1315–7.*
Makiko Sugie et al., "Optical Resolution of DL–Amino Acids with D–Aminoacylase of *Streptomyces*", Agric. Biol. Chem., 44(5), 1089–1095, 1980.
Kubo et al., Deacetylation of PS–5, A New β–Lactam compound III. Enzymological Characterization of L–Amino Acid Acylase and D–Amino Acid Acylase from Pseudomonas SP. 1158, J. Antibiot., 33:556–565, 1980.
Moriguchi et al., "Purification and Characterization of Novel N–Acyl–D–asparate Amidohydrolase from Alcaligenes xylosoxydans subsp. xylosoxydans A–6", Biosci. Biotech. Biochem., 57:1145–1148, 1993.
Sakai et al., "Purification and characterization of N–acyl–D–glutamate deacylase from Alcaligenes xylosoxydans A–6", FEBS, 289:44–46, 1991.
Sakai et al., "Purification and Properties fo D–Aminoacylase from Alcaligenes denitrificans subsp. xylosoxydans MI–4", J. Ferment. Bioeng. 71:79–82, 1991.
Sugie et al., "Purification and Properties of D–Aminoacylase of Streptomyces olivaceus", Agric. Biol. Chem. 42:107–113, 1978.
Wakayama et al., "Primary Structure of N–Acyl–D–Glutamate Amidohydrolase from Alcaligenes xylosoxydans subsp. xylosoxydans A–6", J. Biochem., 118:204–209, 1995.
Wakayama et al., "Cloning and Sequencing of a Gene Encoding D–Aminoacylase from Alcaligenes xylosoxydans subsp. xylosoxydans A–6 and Expression of the Gene in *Escherichia coli*", Biosci. Biotech. Biochem., 59:2115–2119, 1995.

* cited by examiner

*Primary Examiner*—Elizabeth Slobodyansky
*Assistant Examiner*—Christian L. Fronda
(74) *Attorney, Agent, or Firm*—Fish & Richardson P.C.

(57) ABSTRACT

The present invention provides the D-aminoacylase-encoding gene derived from *Hypomyces mycophilus*, a filamentous fungus, the polypeptide encoded by the gene, and the homologues thereof. The D-aminoacylase of the present invention is capable of producing D-tryptophan from N-acetyl-D-tryptophan. D-tryptophan is useful as a medicinal raw material or the like.

3 Claims, No Drawings

D-AMINOACYLASE AND GENE ENCODING THE SAME

CROSS-REFERENCE TO RELATED APPLICATIONS

This is a divisional application and claims priority from U.S. patent application Ser. No. 09/770,517, filed Jan. 26, 2001, now U.S. Pat. No. 6,780,619, which claims priority from Japanese Patent Application Nos. 2000-019080, filed Jan. 27, 2000; and 2000-150578, filed May 22, 2000, the disclosures of which are incorporated herein by reference.

FIELD OF THE INVENTION

The present invention relates to a D-aminoacylase, a gene encoding the D-aminoacylase, and a method for producing D-amino acids using the D-aminoacylase.

BACKGROUND OF THE INVENTION

Enzymes have excellent catalytic functions with substrate specificity, reaction specificity, and stereospecificity. Stereospecificity of enzymes, with some exceptions, are nearly absolute.

Recent precise research has increased the importance of optically active substances for use in drugs, pesticides, feeds, and perfumes. Since optical isomers sometimes have quite different biological activities, techniques for specifically obtaining the isomer are important. For example, D(R)-form thalidomide has no teratogenic activity, but its L(S)-form shows strong teratogenicity. The practical use of thalidomide racemate caused the drug injury incidents by thalidomide. Furthermore, if one enantiomer shows an effective biological activity, the other enantiomer may sometimes have no activity, rather, it may competitively inhibit the activity of the effective enantiomer because of the coexistence of both enantiomers. As a result, the biological activity of the racemate is reduced to half or less of the activity of the effective enantiomer. Accordingly, it is industrially important to obtain (synthesize or optically resolve) optically pure enantiomers.

For this objective, an effective procedure has been used widely to optically resolve racemates synthesized. However, an unnecessary enantiomer is always produced as a by-product with the procedure of resolution after synthesis; a problem has been left unsolved in economizing on raw material. Even if the recovered by-product is reused as a raw material, a definite amount of the by-product is always produced. Therefore, enzymatic optical resolution has drawn attention because it does not produce by-products and a bulk of liquid waste. Enzymatic optical resolution is a method of specifically producing a desired enantiomer by utilizing enzyme specificity. Since unnecessary enantiomers are barely synthesized by this method, it is easy to obtain products of high optical purity. In addition, this method is also advantageous in economizing on raw material.

Generally, L-amino acids are widely and largely utilized in seasonings, food and feed additives, and infusions, and are thus very highly demanded. L-amino acids have been produced mainly by direct fermentation using microorganisms. In addition, optical resolution in which N-acyl-DL-amino acids are hydrolyzed with L-aminoacylases is also a known method for producing L-amino acids. It has been utilized to industrially produce L-amino acids that are difficult to produce by fermentation.

L-aminoacylases are widely found in animals, plants, and microorganisms. They have been purified from various organisms, and their properties have been clarified. N-terminal amino acids of many proteins are considered to be N-acetylated in vivo. L-aminoacylases presumably regenerate N-acetyl-amino acids produced by decomposition of proteins to amino acids. Among L-aminoacylases, acylase that acts on N-acyl-L-glutamic acid is reported to be involved in arginine biosynthesis (Fruth et al., J. Gen. Microb, 125:1, 1981).

In contrast, D-amino acids have not been a subject of interest for a long time because they are nonprotein amino acids. D-amino acids were known to naturally occur only in small cyclic peptides, peptidoglycan of bacterial cell walls, and peptide antibiotics. However, D-amino acids have been demonstrated to be constituents of neuro peptides and to exist as binding forms in tooth enamel, the lens, and cerebral proteins, resulting in investigation of physiological significance and enzymatic synthesis of D-amino acids.

At present, DL-amino acids have been optically resolved by physicochemical, chemical, or enzymatic methods. The enzymatic methods are the most convenient and industrially applicable for, for example, continuously producing L-methionine from N-acetyl-DL-methionine using a bioreactor on which L-aminoacylase is immobilized. D-amino acids may also be produced using hydantoinase. The method consists of two-step enzymatic reactions. The first reaction uses D-specific hydantoinase to convert D,L-5-substituted-hydantoin, which is synthesized at low cost from aldehyde analogues, to a D-carbamyl derivative. The second reaction uses D-amino acid carbamylase.

Another method is known in which D-aminoacylase hydrolyzes N-acetyl-DL-amino acids to produce D-amino acids (Sugie et al., Argric. Biol. Chem., 44:1089, 1980; Tsai et al., J. Enzyme Microb. Technol., 14:384, 1992).

D-tryptophan is one of important D-amino acids used as a medicinal raw material and the like. D-tryptophan can be obtained by deacetylating N-acetyl-DL-tryptophan. However, D-aminoacylase capable of-efficiently catalyzing this reaction in a stereospecific manner is not yet known.

D-aminoacylase was first reported to be found in *Pseudomonas* sp. KT83 isolated from soil by Kameda et al. in 1952 (Kameda et al., Nature, 170:888, 1952). This enzyme hydrolyzed N-benzoyl derivatives of D-phenylalanine, D-tyrosine, and D-alanine. Thereafter, D-aminoacylases were derived from microorganisms below.

Genus *Pseudomonas*
 (Kubo et al., J. Antibiot., 43:550, 1980; Kubo et l., J. Antibiot. 43:556, 1980; Kameda et al., Chem. Pharm. Bull., 26:2698, 1978; Kubo et al., J. Antibiot. 43:543, 1980)

Genus *Streptomyces*
 (Sugie et al., Argric. Biol. Chem., 42:107, 1978; Sugie et al., Argric. Biol. Chem., 44:1089, 1980)

Genus *Alcaligenes*
 (Tsai et al., Appl. Environ. Microbiol., 54:984, 1988; Yang et al., Biosci. Biotech. Biochem., 56:392, 1992; Yang et al., Appl. Environ. Microbiol., 57:2767, 1991; Tsai et al., Microb. Technol., 14:384, 1992; Moriguchi et al., Appl. Environ. Microbiol., 54:2767, 1988; Sakai et al., FEBS, 289:44, 1991; Sakai et al., J. Ferment. Bioeng., 71:79, 1991; Sakai et al., Appl. Environ. Microbiol., 57:2540, 1991; Moriguchi et al., Biosci. Biotech. Biochem., 57:1145, 1993; Kayama et al., J. Biochem., 118:204, 1995; Moriguchi et al., Biosci. Biotech. Biochem., 57:1149, 1993)

Tsai et al. and Moriguchi et al. also clarified the characteristics of D-aminoacylase derived from microorganisms belonging to the genera *Alcaligenes* and *Pseudomonas* and the amino acid and nucleotide sequences of the enzymes.

Moriguchi et al. found, by using different inducers, three types of D-aminoacylases derived from microorganisms belonging to the genera *Alcaligenes* and *Pseudomonas* (Wakayama et al., Biosci. Biotech. Biochem., 59:2115, 1995).

Furthermore, Moriguchi et al. determined the nucleotide sequences of these D-aminoacylases derived from a microorganism belonging to the genus *Alcaligenes* and compared them with L-aminoacylases derived from *Bacillus stereothermophilus*, human, and pig. The result demonstrated that these D-aminoacylases have a low homology with L-aminoacylases (Wakayama et al., Biosci. Biotech. Biochem., 59:2115, 1995).

As to *Actinomycetes*, Sugie et al. reported D-aminoacylase of a microorganism belonging to the genus *Streptomyces* (Sugie et al., Argric. Biol. Chem., 44:1089, 1980). However, the enzyme has not been purified yet, and its characteristics remain unknown.

Any of these known D-aminoacylases exhibit only low activities for N-acetyl-D-tryptophan and cannot be used for synthesizing D-tryptophan. With these points described above as background, it has been demanded to isolate D-aminoacylase capable of producing D-tryptophan stereospecifically using N-acetyl-DL-tryptophan as a substrate as well as a gene encoding the enzyme.

SUMMARY OF THE INVENTION

An objective of the present invention is to provide D-aminoacylase capable of producing D-tryptophan stereospecifically using N-acetyl-DL-tryptophan as a substrate and a gene encoding the enzyme. Another objective of the present invention is to provide uses of the D-aminoacylase and the gene.

In order to achieve the objectives mentioned above, the present inventors have repeatedly isolated many D-aminoacylases from a wide variety of biological species and investigated substrate-specificities of the enzymes. As a result, the inventors have found that a fungus belonging to the genus *Hypomyces* has the activity to produce D-amino acid from N-acetyl-D-amino acid, namely, D-aminoacylase activity. Subsequently, the present inventors have succeeded in separating and purifying D-aminoacylase from the fungus with D-aminoacylase activity by using ammonium sulfate precipitation and various chromatographic methods. In addition, the present inventors elucidated various physicochemical properties such as substrate specificity and thermal stability of the purified D-aminoacylase and have found that it is possible to produce D-amino acids efficiently by incubating the fungus-derived D-aminoacylase with N-acetyl-D-amino acids under proper conditions. It has been confirmed that the D-aminoacylase discovered by the present inventors has especially high enzymatic activity for N-acetyl-D-tryptophan and that the enzyme excels in industrial applicability.

Furthermore, the present inventors have isolated this D-aminoacylase and a gene encoding the enzyme, and revealed their structure. Thus, the present inventors completed the present invention. Previously identified D-aminoacylases have only low enzymatic activities for N-acetyl-D-tryptophan and are thus useless for D-tryptophan synthesis.

Specifically, the present invention relates to a polynucleotide selected from the group consisting of:

(a) a polynucleotide comprising the nucleotide sequence set forth in SEQ ID NO: 1;

(b) a polynucleotide encoding a polypeptide comprising the amino acid sequence set forth in SEQ ID NO: 2;

(c) a polynucleotide hybridizing to a DNA comprising the nucleotide sequence set forth in SEQ ID NO: 1 under a stringent condition, wherein said polynucleotide encodes a polypeptide having activity of a D-aminoacylase having physicochemical properties of (i) and (ii) below; and (d) a polynucleotide encoding a polyopeptide having the amino acid sequence set forth in SEQ ID NO: 2 in which one or more amino acid are substituted, deleted, inserted, and/or added, wherein said polynucleotide encodes a polypeptide having activity of a D-aminoacylase having physicochemical properties of (i) and (ii) below (i) action: the enzyme acts on N-acetyl-D-amino acids to produce the corresponding D-amino acids and (ii) substrate specificity: the enzyme acts on N-acetyl-D-tryptophan, N-acetyl-D-phenylalanine, N-acetyl-D-valine, N-acetyl-D-leucine, and N-acetyl-D-methionine, but not on N-acetyl-L-tryptophan, N-acetyl-L-phenylalanine, N-acetyl-L-valine, N-acetyl-L-leucine, or N-acetyl-L-methionine.

The present invention also relates to a polypeptide encoded by the above polynucleotide.

Furthermore, the present invention features a vector comprising the above polynucleotide, a transformant expressively carrying the polynucleotide, or the vector, and a method of producing the polypeptide, which comprises culturing the transformant and recovering the expression product. The transformant is preferably derived from *E. coli*.

Another feature of the present invention is a polynucleotide hybridizing to the polynucleotide set forth in SEQ ID NO: 1 or the complementary strand thereof, wherein said polypeptide comprises at least 15 nucleotides. This polynucleotide can be used as a primer for synthesizing the above-mentioned polynucleotide or used as a probe for detecting the polynucleotide.

Still another feature of the present invention is a method for synthesizing D-amino acids, which comprises contacting the above-mentioned polypeptide or the transformant with N-acyl-DL-amino acid represented by the formula (I) or its salt:

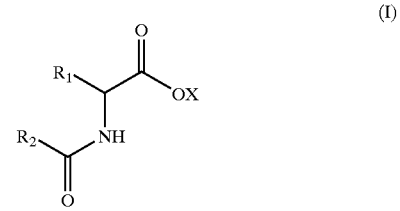

(I)

wherein $R_1$ and $R_2$ may be identical or different and each represents a hydrogen atom or a substituted or unsubstituted hydrocarbon group; provided that $R_2$ does not represent a hydrogen atom; and X is H, $NH_4$, or a metal ion. In the formula (I), $R_1$ and $R_2$ preferably each represents an alkyl, alkenyl, alkynyl, cycloalkyl, aryl, or aralkyl group, or the derivative thereof. More preferably, $R_1$ is an β-methylindolyl, benzyl, thiomethylethyl, isopropyl, or 2-methylpropyl group and $R_2$ is a methyl, chloromethyl, phenyl, or aminomethyl group.

"D-aminoacylase" used herein means an enzyme reacting with an N-acyl-D-amino acid to catalyze the production of an organic acid and a D-amino acid.

DETAILED DESCRIPTION OF THE INVENTION

The present invention relates to an isolated polynucleotide encoding a D-aminoacylase and homologues thereof.

An "isolated polynucleotide" is a polynucleotide the structure of which is not identical to that of any naturally occurring polynucleotide or to that of any fragment of a naturally occurring genomic polynucleotide spanning more than three separate genes. The term therefore includes, for example, (a) a DNA which has the sequence of part of a naturally occurring genomic DNA molecule in the genome of the organism in which it naturally occurs; (b) a polynucleotide incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are polynucleotides of DNA molecules present in mixtures of different (i) DNA molecules, (ii) transfected cells, or (iii) cell clones; e.g., as these occur in a DNA library such as a cDNA or genomic DNA library.

The polynucleotide encoding the D-aminoacylase of the present invention comprises, for example, the nucleotide sequence of SEQ ID NO: 1. The nucleotide sequence of SEQ ID NO: 1 encodes a polypeptide comprising the amino acid sequence of SEQ ID NO: 2. The polypeptide comprising this amino acid sequence constitutes preferred embodiments of the D-aminoacylase of the present invention. An amino acid is not always encoded by a single codon; because of degeneracy, there can be multiple codons corresponding to an amino acid, which is well known to those skilled in the art. Therefore, nucleotide sequences encoding the amino acid sequence shown in SEQ ID NO: 2 comprise not only the nucleotide sequence of SEQ ID NO: 1 but also any nucleotide sequence comprising other different codons as long as it encodes the amino acid sequence of SEQ ID NO: 2.

The homologue of the polynucleotide encoding the D-aminoacylase of the present invention includes a DNA encoding a polypeptide having enzymatic activity to produce D-amino acid from N-acyl-D-amino acid as well as comprising the amino acid sequence of SEQ ID NO: 2 or the amino acid sequence of SEQ ID NO: 2 in which one or more amino acids are deleted, substituted, inserted, and/or added. One skilled in the art can readily obtain such a homologue of the polynucleotide by properly introducing substitution, deletion, insertion, and/or addition mutation into the DNA of SEQ ID NO: 1 by site-specific mutagenesis (Nucleic Acid Res., 10:6487 (1982), Methods in Enzymol., 100:448 (1983); Molecular Cloning 2nd Ed., Cold Spring Harbor Laboratory Press (1989), PCR: A Practical Approach, IRL Press, pp. 200 (1991)). Alternatively, although the nucleotide sequence of SEQ ID NO: 1 is derived from strain IFO6785 of *Hypomyces mycophilus* (this strain is recited in the List of Cutures 10th edition (1996) published by Institute of Fermentation Research, Osaka (IFO) and is available from IFO), any polynucleotides encoding polypeptides having the functionally equivalent enzymatic activity, which can be obtained from other species based on the information disclosed in the present invention, are included in the present invention. These homologues can be naturally occurring polynucleotides.

The polynucleotide of the present invention may be DNA or RNA; as to its structure, the polynucleotide may be single-stranded or a duplex with two strands complementary to each other. There is no restriction on length of the polynucleotide of the present invention, but it preferably comprises at least 15 nucleotides. Moreover, the polynucleotide of the present invention may comprise naturally occurring or artificial nucleotide derivatives, or may be modified with a variety of labels or tags. In addition, the polynucleotide of the present invention includes those derived from genomic DNA or cDNA as well as artificially synthesized ones.

The homologue of the polynucleotide of the present invention includes polynucleotides hybridizing under stringent conditions to the polynucleotide comprised in the nucleotide sequence of SEQ ID NO: 1 as well as encoding a polypeptide having D-aminoacylase activity to produce D-amino acids from N-acyl-D-amino acid. The "polynucleotide hybridizing under stringent conditions" means a polynucleotide hybridizing to a probe nucleotide that has one or more segments of at least 20 consecutive nucleotides, preferably at least 30 consecutive nucleotides, for example, 40, 60, or 100 consecutive nucleotides, arbitrarily selected from the sequence shown in SEQ ID NO: 1, by using, for example, ECL Direct Nucleic Acid Labeling and Detection System (Amersham-Pharmacia Biotech) under conditions recommended in the attached manual (washing with the primary wash buffer containing 0.5×SSC at 42° C.).

Furthermore, the homologue of the polynucleotide of the present invention includes a DNA encoding a polypeptide exhibiting percent identity of at least 70%, preferably at least 80% or 90%, more preferably 95% or more to the amino acid sequence of SEQ ID NO: 2. As used herein, "percent identity" of two amino acid sequences or of two nucleic acids is determined using the algorithm of Karlin and Altschul (Proc. Natl. Acad. Sci. USA, 87:2264–2268, 1990) modified as in Karlin and Altschul (Proc. Natl. Acad. Sci. USA, 90:5873–5877, 1993). Such an algorithm is incorporated into the NBLAST and XBLAST programs of Altschul et al. (J. Mol. Biol., 215:403–410, 1990). BLAST nucleotide searches are performed with the NBLAST program, score= 100, wordlength=12. Homology search of protein can readily be performed, for example, in DNA Databank of JAPAN (DDBJ), by using the FASTA program, BLAST program, etc. BLAST protein searches are performed with the XBLAST program, score=50, wordlength=3. Where gaps exist between two sequences, Gapped BLAST is utilized as described in Altsuchl et al. (Nucleic Acids Res., 25:3389–3402, 1997). When utilizing BLAST and Gapped BLAST programs, the default parameters of the respective programs (e.g, XBLAST and NBLAST) are used. See http://www.ncbi.nlm.nih.gov.

The present invention encompasses a substantially pure polypeptide having the amino acid sequence of SEQ ID NO: 2 and having enzymatic activity to produce D-amino acids from N-acyl-D-amino acid as well as homologues of the polypeptide. The polypeptide comprising the amino acid sequence of SEQ ID NO: 2 constitutes preferred embodiments of the polypeptide of the present invention.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example by column chromatography, polyacrylamide gel elecrophoresis, or HPLC analysis.

The homologue of the polypeptide of the present invention comprises the amino acid sequence of SEQ ID NO: 2 in which one or more amino acids are deleted, substituted, inserted, and/or added. One skilled in the art can readily obtain a polynucleotide encoding such a homologue of the polypeptide of the present invention by properly introducing substitution, deletion, insertion, and/or addition mutation into the DNA of SEQ ID NO: 1 by site-specific mutagenesis (Nucleic Acid Res., 10:6487, 1982; Methods in Enzymol., 100:448, 1983; Molecular Cloning 2nd Ed., Cold Spring Harbor Laboratory Press (1989), PCR: A Practical Approach IRL Press pp. 200 (1991)) or the like. The homologue of the polypeptide of SEQ ID NO: 2 is available by introducing a polynucleotide encoding the polypeptide homologue into a host and expressing it in the host.

The number of amino acids that are mutated is not particularly restricted, as long as the D-aminoacylase activity is maintained. Normally, it is within 50 amino acids, preferably within 30 amino acids, more preferably within 10 amino acids, and even more preferably within 3 amino acids. The site of mutation may be any site, as long as the D-aminoacylase activity is maintained.

An amino acid substitution is preferably mutated into different amino acid(s) in which the properties of the amino acid side-chain are conserved. A "conservative amino acid substitution" is a replacement of one amino acid residue belonging to one of the following groups having a chemically similar side chain with another amino acid in the same group. Groups of amino acid residues having similar side chains have been defined in the art. These groups include amino acids with basic side chains (e.g., lysine, arginine, histidine), acidic side chains (e.g., aspartic acid, glutamic acid), uncharged polar side chains (e.g., glycine, aspargine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Furthermore, the homologue of the D-polypeptide of the present invention includes a polypeptide exhibiting percent identity of at least 70%, preferably at least 80% or 90%, more preferably 95% or more to the amino acid sequence of SEQ ID NO: 2. Determination of percent identity of two amino acid sequences or of two nucleic acids and homology search can be performed as described above.

The polynucleotide encoding the polypeptide of the present invention may be isolated, for example, by using the following procedure. Specifically, a genomic library or cDNA library from a fungus capable of producing D-aminoacylase is screened by using, as a probe, a DNA comprising a nucleotide sequence segment selected from the nucleotide sequence of SEQ ID NO: 1, thereby isolating the polynucleotide of the present invention. Since the nucleotide sequence of SEQ ID NO: 1 is derived from IFO6785 strain of *Hypomyces mycophilus*, the polynucleotide of the present invention sequence can be isolated from a library prepared from the strain. A homologue of the polynucleotide of the present invention can also be isolated by using a library derived from the related fungus or other fungal species.

It is possible to prepare a genomic library of a fungus according to a known method. Namely, fungal cells cultured were first harvested, and then lysed by a physical or enzymatic means. A specific example of such lysis methods is cell-wall disruption by freezing the fungal cells. Subsequently, the nuclear fraction collected is subjected to phenol/chloroform extraction, and the resulting nucleic acid is digested randomly with restriction enzyme(s) or the like. Inserting the genomic fragments obtained by random digestion into proper cloning vector produces a genomic library.

On the other hand, it is possible to prepare a cDNA library according to the following procedure. For example, mRNA is extracted and purified from the frozen fungal cells by using a QuickPrep mRNA Purification Kit (Amersham-Pharmacia Biotech) according to the protocol. The resulting mRNA is used as a template to prepare a cDNA library according to the method of Gubler and Hoffman (Gene, 25:263–269, 1983). Specifically, a cDNA is synthesized by using an oligo(dT) primer and reverse transcriptase. The cDNA is inserted into a proper plasmid to give a cDNA library.

A probe is allowed to hybridize to the library, preferably under the stringent conditions as described above. The positive clones are collected and subjected to sequencing analysis to clarify whether or not the clones correspond to the polynucleotide of the present invention. If the isolated polynucleotide does not completely contain the protein-coding region, then the complete DNA of the present invention can be obtained by designing PCR primers, based on the sequence already obtained, to extend the DNA outward, by digesting, with an appropriate restriction enzyme(s), the chromosomal DNA of the strain producing the enzyme of interest and then, by performing inverse PCR (Genetics, 120:621–623, 1988) using the self-ligated circular DNA as a template; or alternatively by using RACE method (Rapid Amplification of cDNA End; "Experimental manual for PCR" pp. 25–33, HBJ Press).

Furthermore, the polynucleotide of the present invention may be obtained by PCR using primers designed based on the nucleotide sequence of SEQ ID NO: 1 or SEQ ID NO: 25. Specifically, PCR using the above-mentioned genomic or cDNA library as a template amplifies fragments with a target size. The fragments are recovered and incorporated into a proper cloning vector and are screened to isolate the polynucleotide of the present invention. Not only the polynucleotide of SEQ ID NO: 1 but also highly homologous sequences thereto can be synthesized by using degenerated primers as PCR primers. Those skilled in the art routinely design, based on a given nucleotide sequence, such primers to amplify the sequence as well as such degenerated primers to amplify a homologue of the sequence. The polynucleotide of the present invention includes not only the genomic DNA and cDNA cloned by the above-mentioned methods but also chemically synthesized DNA.

The isolated polynucleotide encoding the D-aminoacylase of the present invention is inserted into a known expression vector to provide a D-aminoacylase-expressing vector. Further, by culturing cells transformed with the expression vector, the D-aminoacylase of the present invention can be obtained from the transformed cells.

There is no restriction on the microorganism to be transformed for D-aminoacylase expression in the present invention, as far as the organism is capable of being transformed with the vector containing the recombinant polynucleotide encoding the polypeptide with D-aminoacylase activity and capable of expressing D-aminoacylase activity. Available microorganisms are those for which host-vector systems are available and include, for example:

bacteria such as the genus *Escherichia*, the genus *Bacillus*, the genus *Pseudomonas*, the genus *Serratia*, the genus *Brevibacterium*, the genus *Corynebacterium*, the genus *Streptococcus*, and the genus *Lactobacillus*;

actinomycetes such as the genus *Rhodococcus* and the genus *Streptomyces*; yeasts such as the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Hansenula*, the genus *Pichia*, and the genus *Candida*; and fungi such as the genus *Neurospora*, the genus *Aspergillus*, the genus *Cephalosporium*, and the genus *Trichoderma*; etc.

Procedure for preparation of a transformant and construction of a recombinant vector suitable for a host can be carried out by employing techniques that are commonly used in the fields of molecular biology, bioengineering, and genetic engineering (for example, see Sambrook et al., "Molecular Cloning", Cold Spring Harbor Laboratories). In order to express, in a microorganism, the gene encoding the D-aminoacylase of the present invention, it is necessary to introduce the DNA into a plasmid vector or phage vector that is stable in the microorganism and to let the genetic information transcribed and translated. To do so, a promoter, a unit for regulating transcription and translation, is placed upstream of the 5' end of the DNA of the present invention, and preferably a terminator is placed downstream of the 3' end of the DNA. The promoter and the terminator should be functional in the microorganism to be utilized as a host. Available vectors, promoters, and terminators for the above-mentioned various microorganisms are described in detail in "Fundamental Course in Microbiology (8): Genetic Engineering", Kyoritsu Shuppan, specifically for yeasts, in "Adv. Biochem. Eng. 43, 75–102 (1990)" and "Yeast 8, 423–488 (1992)."

For example, for the genus *Escherichia*, in particular, for *Escherichia coli*, available plasmids include pBR series and pUC series plasmids; available promoters include promoters derived from lac (derived from β-galactosidase gene), trp (derived from the tryptophan operon), tac and trc (which are chimeras of lac and trp), $P_L$ and $P_R$ of λ phage, etc. Available terminators are derived from trpA, phages, rrnB ribosomal RNA, etc.

For the genus *Bacillus*, available vectors are pUB110 series and pC194 series plasmids; the vectors can be integrated into host chromosome. Available promoters and terminators are derived from apr (alkaline protease), npr (neutral protease), amy (α-amylase), etc.

For the genus *Pseudomonas*, there are host-vector systems developed for *Pseudomonas putida* and *Pseudomonas cepacia*. A broad-host-range vector, pKT240, (containing RSF1010-derived genes required for autonomous replication) based on TOL plasmid, which is involved in decomposition of toluene compounds, is available; a promoter and a terminator derived from the lipase gene (Unexamined Published Japanese Patent Application (JP-A) No. Hei 5-284973) are available.

For the genus *Brevibacterium*, in particular, for *Brevibacterium lactofermentum*, available plasmid vectors include pAJ43 (Gene, 39:281, 1985). Promoters and terminators used for *Escherichia coli* can be utilized without any modification for *Brevibacterium*.

For the genus *Corynebacterium*, in particular, for *Corynebacterium glutamicum*, plasmid vectors such as pCS11 (JP-A No. Sho 57-183799) and pCB101 (Mol. Gen. Genet., 196:175, 1984) are available.

For the genus *Streptococcus*, plasmid vectors such as pHV1301 (FEMS Microbiol. Lett., 26:239, 1985) and pGK1 (Appl. Environ. Microbiol., 50:94, 1985) can be used.

For the genus *Lactobacillus*, plasmid vectors such as pAMβ1 (J. Bacteriol., 137:614, 1979), which was developed for the genus *Streptococcus*, can be utilized; and promoters that are used for *Escherichia coli* are also usable.

For the genus *Rhodococcus*, plasmid vectors isolated from *Rhodococcus rhodochrous* are available (J. Gen. Microbiol., 138:1003, 1992).

For the genus *Streptomyces*, plasmids can be constructed in accordance with the method as described in "Genetic Manipulation of *Streptomyces*: A Laboratory Manual" (Cold Spring Harbor Laboratories (1985)) by Hopwood et al. In particular, for *Streptomyces lividans*, pIJ486 (Mol. Gen. Genet., 203:468–478, 1986), pKC1064 (Gene, 103:97–99, 1991), and pUWL-KS (Gene, 165:149–150, 1995) are usable. The same plasmids can also be utilized for *Streptomyces virginiae* (Actinomycetol., 11:46–53, 1997).

For the genus *Saccharomyces*, in particular, for *Saccharomyces cerevisiae*, YEp series, YEp series, YCp series, and YIp series plasmids are available; integration vectors (refer EP 537456, etc.), which are integrated into chromosome via homologous recombination with multicopy-ribosomal genes, allow to introduce a gene of interest in multicopy and the gene incorporated is stably maintained in the microorganism; and thus, these types of vectors are highly useful. Available promoters and terminators are derived from genes encoding ADH (alcohol dehydrogenase), GAPDH (glyceraldehyde-3-phosphate dehydrogenase), PHO (acid phosphatase), GAL (β-galactosidase), PGK (phosphoglycerate kinase), ENO (enolase), etc.

For the genus *Kluyveromyces*, in particular, for *Kluyveromyces lactis*, available plasmids are those such as 2-μm plasmids derived from *Saccharomyces cerevisiae*, pKD1 series plasmids (J. Bacteriol., 145:382–390, 1981), plasmids derived from pGK11 and involved in the killer activity, KARS (*Kluyveromyces* autonomous replication sequence) plasmids, and plasmids (refer EP 537456, etc.) capable of being integrated into chromosome via homologous recombination with the ribosomal DNA. Promoters and terminators derived from ADH, PGK, and the like are available.

For the genus *Schizosaccharomyces*, it is possible to use plasmid vectors comprising ARS (autonomous replication sequence) derived from *Schizosaccharomyces pombe* and auxotrophy-complementing selectable markers derived from *Saccharomyces cerevisiae* (Mol. Cell. Biol., 6:80, 1986). Promoters such as ADH promoter derived from *Schizosaccharomyces pombe* are usable (EMBO J., 6:729, 1987). In particular, pAUR224 is commercially available from TaKaRa Shuzo Co., Ltd.

For the genus *Zygosaccharomyces*, plasmids originating from those such as pSB3 (Nucleic Acids Res., 13:4267, 1985) derived from *Zygosaccharomyces rouxii* are available; it is possible to use promoters such as PHO5 promoter derived from *Saccharomyces cerevisiae* and GAP-Zr (Glyceraldehyde-3-phosphate dehydrogenase) promoter (Agri. Biol. Chem., 54:2521, 1990) derived from *Zygosaccharomyces rouxii*.

For the genus *Hansenula*, host-vector systems have been developed for *Hansenula polymorpha*. *Hansenula polymorpha*-derived autonomous replication sequences, HARS1 and HARS2, may be utilized as vectors, but the replication sequences are relatively unstable, and accordingly multicopy integration into chromosome is an effective way to ensure stable introduction of genes (Yeast, 7:431–443, 1991). Promoters such as that of the AOX (alcohol oxidase) gene, of which expression is induced by methanol or the like, and a promoter from the FDH (formic acid dehydrogenase) are available.

For the genus *Pichia*, host-vector systems originating from autonomous replication sequences (PARS 1, PARS2) derived from *Pichia* have been developed (Mol. Cell. Biol., 5:3376, 1985), and it is possible to employ a highly efficient promoter such as or methanol-inducible AOX promoter, which is available for high-cell-density-culture (Nucleic Acids Res., 15:3859, 1987).

For the genus *Candida*, host-vector systems have been developed for *Candida maltosa, Candida albicans, Candida*

*tropicalis, Candida utilis*, etc. An autonomous replication sequence originating from *Candida maltosa* has been cloned (Agri. Biol. Chem., 51:1587, 1987), and a vector using the sequence has been developed for *Candida maltosa*. Further, a chromosome-integration vector with a highly efficient promoter unit has been developed for *Candida utilis* (JP-A No. Hei. 08-173170).

For the genus *Aspergillus, Aspergillus niger* and *Aspergillus oryzae* have intensively been studied among fungi, and thus plasmid vectors and chromosome-integration vectors are available, as well as promoters derived from an extracellular protease gene and amylase gene (Trends in Biotechnology, 7:283–287, 1989).

For the genus *Trichoderma*, host-vector systems have been developed for *Trichoderma reesei*, and promoters such as that derived from an extracellular cellulase gene are available (Biotechnology, 7:596–603, 1989).

There are various host-vector systems developed for plants and animals other than microorganisms; in particular, the systems include those of insect such as silkworm (Nature, 315:592–594, 1985), and plants such as rapeseed, maize, potato, etc. These systems are preferably employed to express a large amount of foreign protein.

It is possible to cultivate the host microorganism transformed with the polynucleotide encoding the D-aminoacylase of the present invention according to known information. The D-aminoacylase of the present invention can be recovered from the culture. Either synthetic or natural media can be used as long as they contain proper amounts of the carbon source, nitrogen source, inorganic materials, and other nutrients. The culture media may be either liquid or solid.

More specifically, examples of the carbon source include sugars such as glucose, fructose, maltose, galactose, starch, starch hydrolysate, molasses, and blackstrap molasses; natural carbohydrates such as wheat, barley, and corn; alcohols such as glycerol, methanol, and ethanol; fatty acids such as acetic acid, gluconic acid, pyruvic acid, and citric acid; hydrocarbons such as normal paraffin; and amino acids such as glycine, glutamine, and asparagine. One or more of the above carbon sources are used depending on assimilability of the fungus used. Examples of the nitrogen sources include organic nitrogen-containing compounds such as meat extract, peptone, yeast extract, soybean hydrolysate, milk casein, casamino acid, various amino acids, corn steep liquor, and other hydrolysates of animals, plants, and microorganisms; and inorganic nitrogen-containing compounds such as ammonia, ammonium salts such as ammonium nitrate, ammonium sulfate, ammonium chloride, nitrates such as sodium nitrate, and urea. One or more of the above nitrogen sources are used depending on assimilability of the fungus.

Furthermore, a minute amount of one or more inorganic salts can be used. Examples thereof include phosphates; hydrochlorides; nitrates; acetates; or similar salts of magnesium, manganese, potassium, calcium, sodium, copper, or zinc. Antifoaming agents, such as vegetable oil, surfactants, or silicon, may be added to the culture medium.

Culturing can be performed in the liquid medium containing the above-described ingredients using the usual culture methods, such as shaking culturing, aerobic agitation culturing, continuous culturing, or fed-batch culturing.

Culturing conditions may be properly selected depending upon the fungal strain and culture method, and are not particularly limited as long as the fungi used can proliferate to produce D-aminoacylase. It is usually preferred to adjust the initial pH to 4 to 10, preferably 6 to 8, and to culture at a temperature of 15 to 50° C., preferably 25 to 35° C.

The foreign gene contained in the transformant is induced under appropriate conditions given in a growth phase or after full growth. For example, in the case of lac promoter, addition of IPTG induces the expression of the foreign gene that is connected downstream of the promoter. As for a temperature-sensitive promoter, the culture is performed at a temperature required for the expression.

As described above, when previously reported D-aminoacylase-producing bacteria are used for the synthesis of D-amino acids, a substance responsible for inducing the enzyme often inhibits the production of the reaction product. On the other hand, if genetic recombinants are used for the synthesis of D-amino acids, an inducing agent or temperature control responsible for the expression of the gene does not inhibit the production of the reaction product in most cases.

The culturing time is also not particularly limited as long as a sufficient amount of fungal cells having the D-aminoacylase activity can be obtained. The culturing is usually performed for 1 to 14 days, preferably for 1 to 3 days. The D-Aminoacylase produced and accumulated with gene expression can be recovered and isolated by the following methods.

When D-aminoacylase is intracellularly produced, the fungal cells are collected by the method such as filtration or centrifugation after the culturing and washed with buffer, physiological saline, etc. The enzyme can then be extracted by disrupting the fungal cells using physical means such as freeze-thawing, ultrasonication, compression, osmotic treatment, or trituration; using biochemical means such as cell wall lysis with lysozyme; or using chemical means such as surfactant treatment. One or more of these treatments can be combined. The crude D-aminoacylase thus obtained can be purified by a single or combined fractionation means including salting out; fractional precipitation with organic solvents, etc.; various chromatographies such as salting-out chromatography, ion-exchange chromatography, gel filtration chromatography, hydrophobic chromatography, dye chromatography, hydroxylapatite chromatography, or affinity chromatography; and electrophoresis such as isoelectric focusing and native electrophoresis. The above chromatographies can be performed using open columns or by means of medium-pressure or high-performance liquid chromatography (HPLC).

For example, the fungal cells collected by filtration or centrifugation are frozen, suspended in a buffer after grinding, and triturated using a Dyno Mill to obtain a D-aminoacylase extract. The extract is then successively subjected to salting-out using ammonium sulfate, ion-exchange chromatography on DEAE-Sepharose FF, hydrophobic chromatography on Phenyl-Sepharose FF, Sephadex 200 gel filtration chromatography, and MonoQ ion-exchange chromatography. The enzyme thus purified can be detected as a single protein band by SDS-polyacrylamide gel electrophoresis.

The D-aminoacylase of the present invention is thus purified and comprises the amino acid sequence of SEQ ID NO: 2. The enzyme has the physico-chemical properties (a) to (f) below:

(a) action: the enzyme acts on N-acetyl-D-amino acids to produce the corresponding D-amino acids;

(b) molecular weight: the molecular weight of the enzyme is about 64,000 daltons determined by SDS-polyacrylamide gel electrophoresis, and about 56,000 daltons determined by gel filtration chromatography on Superdex 200 Hi-Load 6/16 (Amersham Pharmacia Biotech);

(c) substrate specificity: the enzyme acts on N-acetyl-D-tryptophan, N-acetyl-D-phenylalanine, N-acetyl-D-valine, N-acetyl-D-leucine, and N-acetyl-D-methionine, but not on N-acetyl-L-tryptophan, N-acetyl-L-phenylalanine, N-acetyl-L-valine, N-acetyl-L-leucine, or N-acetyl-L-methionine;

(d) thermostability: when heated at pH 9.5 for 30 min, the enzyme is stable at 45° C., but inactivated at 60° C. or higher;

(e) optimal temperature: for the reaction at pH 7.5, the enzyme activity is optimal at about 45° C.; and (f) stabilizer: the enzyme activity is stabilized by reducing agents and activated by $ICH_2CONH_2$.

The substrate specificity of the D-aminoacylase of the present invention can be tested by the following procedure. For example, an enzyme solution (1 μl) is mixed and incubated with 50 mM Tris-HCl (pH 7.5) buffer (total volume: 1.0 ml) containing 20 mM substrate (various N-acetyl-D-amino acids) at 30° C. for 20 minutes. By measuring the amounts of amino acid synthesized by this reaction, enzymatic activities for respective substrates can be compared with each other. Assay for amino acid is performed by TNBS (trinitrobenzenesulfonic acid) method or HPLC method. For example, D-tryptophan, which may be used as a standard product in the reaction, is assayed for a comparison of enzymatic activity; by taking the amount of enzyme required for the production of 1 μmol D-tryptophan as 1 unit (or U), the reactivity is compared between different enzymes or is compared with the reactivity assayed for other types of amino acids.

Based on such analytical results, it has been confirmed that the D-aminoacylase of the present invention, which comprises the amino acid sequence of SEQ ID NO: 2, very efficiently catalyzes the reaction with N-acetyl-D-phenylalanine and N-chloroacetyl-D-phenylalanine.

It has also been confirmed that the enzyme efficiently catalyzes the reaction with N-acetyl-D-tryptophan, N-acetyl-D-methionine, and N-acetyl-D-leucine.

It has also been confirmed that the enzyme catalyzes the reaction with N-acetyl-D-valine as well.

On the other hand, it has been found that the enzyme has substantially no catalytic activity for the substrates, N-acetyl-L-phenylalanine, N-acetyl-L-tryptophan, N-acetyl-L-methionine, N-acetyl-L-valine, and N-acetyl-L-leucine. Herein, "have substantially no catalytic activity" means that a detectable amount of the reaction product is not produced under the reaction conditions described above.

D-aminoacylase of the present invention is capable of acting on various N-acyl-D-amino acids to yield the corresponding D-amino acids, enabling the industrially advantageous production of D-amino acids. For example, D-amino acid can be selectively produced by reacting D-aminoacylase of this invention with N-acyl-DL-amino acid, a mixture of D- and L-enantiomers.

N-acyl-DL-amino acids used in the present invention are not particularly limited and can be selected from a wide variety of compounds. A typical N-acyl-DL-amino acid can be represented by the formula (I):

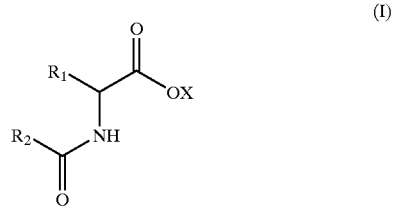

(I)

where $R_1$ and $R_2$ may be identical or different and each represents a hydrogen atom or a substituted or unsubstituted hydrocarbon group, provided that $R_2$ does not represent a hydrogen atom; and X is H, $NH_4$, or a metal ion.

The hydrocarbon group represented by $R_1$ and $R_2$ is preferably alkyl, alkenyl, alkynyl, cycloalkyl, aryl, or aralkyl, or the derivative thereof. The derivative used herein means those of alkyl, alkenyl, alkynyl, cycloalkyl, aryl, or aralkyl substituted with alkyl, alkenyl, alkynyl, cycloalkyl, aryl, aralkyl, hydroxy, halogen, amino, thio, methylthio, or the like; or aryl or aralkyl of which aromatic ring moiety is a heterocycle comprising one or more nitrogen(s) or sulfur(s).

Specific examples of the hydrocarbon group contain from 1 to 10 carbon atoms, including linear or branched alkyl having 1 to 6 carbon atoms, such as methyl, ethyl, n-propyl, i-propyl, n-butyl, i-butyl, sec-butyl, t-butyl, n-pentyl, i-pentyl, n-hexyl, etc.; alkenyl having 1 to 6 carbon atoms such as ethenyl, 1-propenyl, 2-propenyl, 1-butenyl, 2-butenyl, 2-pentenyl, 4-pentenyl, 1-hexenyl, 3-hexenyl, 5-hexenyl, etc.; alkynyl having 1 to 6 carbon atoms such as ethynyl, 1-propynyl, 2-pentynyl, etc.; aryl such as phenyl, naphthyl, etc.; cycloalkyl such as cyclopropyl, cyclobutyl, cyclopentyl, cyclohexyl, etc. The substituent of the hydrocarbon group for $R_1$ and $R_2$ includes halogen; alkyl as defined above; alkenyl as defined above; alkynyl as defined above; aryl as defined above; heterocyclic such as piridyl, indole, quinolyl, etc.; amino; hydroxyl; thio; etc. $R_1$ is preferably β-methylindolyl (for N-acyl-DL-tryptophan), benzyl (for N-acyl-DL-phenylalanine), thiomethylethyl (for N-acyl-DL-methionine), isopropyl (for N-acyl-DL-valine), or 2-methylpropyl (for N-acyl-DL-leucine). $R_2$ is preferably methyl, chloromethyl, phenyl, or aminomethyl, which may be substituted with the above substituent(s). The metal ion represented by X includes sodium, patassium, etc. Preferable examples of N-acyl-DL-amino acids are N-acetyl-DL-amino acids such as N-acetyl-DL-methionine, N-acetyl-DL-valine, N-acetyl-DL-tryptophan, N-acetyl-DL-asparagine, N-acetyl-DL-phenylalanine, N-acetyl-DL-alanine, and N-acetyl-DL-leucine.

N-acetyl-DL-amino acids can be used in the form of a salt such as a sodium salt or a potassium salt.

D-Aminoacylase used for producing D-amino acid in the present invention includes a partially purified enzyme as well as the purified one. Besides these enzyme proteins, the D-aminoacylase-producing transformant itself can also be used in the present invention. Namely, D-amino acid can be produced by directly reacting the transformant capable of producing D-aminoacylase with N-acetyl-DL-amino acid. The transformant can be used in the form of the culture, cells separated from the culture medium by filtration, centrifugation or the like, or cells resuspended in buffer, water, or the like after they are separated by centrifugation and washed. The separated cells can be used in a state as they are recovered, as their disrupts, as treated with acetone or toluene, or as lyophilizate. When the enzyme is extracellularly produced, the culture medium of the transformant can also be used after it is separated from the transformant by the usual methods.

D-aminoacylase or the transformant capable of producing the enzyme is reacted with N-acyl-D-amino acid under conditions suitable for the activity and stability of D-aminoacylase, and for the reactivity of the transformant. Some D-aminoacylases are inhibited by divalent metal ions such as $Zn^{2+}$, $Ni^{2+}$, and $Co^{2+}$. To prevent these metal ions from inhibiting the activity, a chelating reagent such as EDTA can be added.

Though the concentration of the substrate, N-acetyl-DL-amino acid, is not particularly limited, it is usually employed at a concentration of about 0.1 to 30 w/v %. Use of a large amount of D-aminoacylase often accelerates the reaction rate, and the enzyme is usually used in the amount of about 1 to 1,000 U/ml. One unit of the enzyme is defined as the amount of the enzyme to produce 1 μmol of D-tryptophan at 30° C. in 1 min when the enzyme is reacted with N-acetyl-D-tryptophan as the substrate. It is preferred to maintain the reaction temperature at which the D-aminoacylase activity is exhibited, 30 to 50° C. It is preferred to maintain the reaction pH at which the D-aminoacylase is active, for example, pH4 to 10. The reaction can be performed with or without stirring.

In general, an enzyme or a microorganism can be stabilized by immobilization. Immobilization can be done by a known method on a suitable carrier such as polyacrylamide gel, sulfur-containing polysaccharide gel (carrageenan gel), alginic acid gel, or agar gel. Time required for the reaction with the immobilized enzyme or microorganism depends on the amounts of both D-aminoacylase and substrate. One skilled in the art can empirically optimize these conditions as the most ideal ones. Usually, ten- to one hundred-hour reaction efficiently produces a desired reaction product.

The D-amino acids produced can be recovered from the reaction mixture by a known method such as direct crystallization by concentration or isoelectric precipitation, ion exchange resin treatment, membrane filtration, or the like. For example, D-tryptophan produced using N-acetyl-DL-tryptophan as a substrate can be purified as follows. After the enzymatic reaction, the reaction mixture is contacted with strongly acidic cation exchange resin to adsorb D-tryptophan. The resin was washed with water and D-tryptophan was eluted with 0.5 N aqueous ammonia. After the eluate was concentrated, the thus-obtained crude crystalline powder of D-tryptophan is dissolved in a small amount of 50% hot ethanol, decolorized with activated charcoal, and cooled to obtain purified crystals of D-tryptophan.

In the method of the present invention, D-valine can be purified as follows. After the enzymatic reaction, the microbial cells are removed by centrifugation or the like, and the resulting supernatant is adjusted to pH 1 by adding 6N hydrochloric acid. The precipitated N-acetyl-L-valine is removed by centrifugation. The supernatant is treated with activated charcoal, adjusted to pH 7.0, then added to an $H^+$-type strongly acidic cation exchanger (Amberlite IR-120B). Elution is performed with 5% aqueous ammonia, and the resulting eluate is dried at 80° C. under reduced pressure, thereby obtaining purified D-valine.

The present invention discloses identification of D-aminoacylase derived from *Hypomyces mycophilus*, a filamentous fungus, and the structure of the gene encoding the enzyme. Based on the determined nucleotide sequence of the gene, recombinant polypeptide of the D-aminoacylase of the present invention can be manufactured at a low cost and in large quantities.

The D-aminoacylase of the present invention exhibits high enzymatic activity for N-acetyl-D-tryptophan, and therefore, D-tryptophan can be produced efficiently. So far, there have been no D-aminoacylases showing high enzymatic activity for N-acetyl-D-tryptophan. D-tryptophan, which can be produced by using the D-aminoacylase of the present invention, is a useful compound as a medicinal raw material or the like.

Any patents, patent applications, and publications cited herein are incorporated by reference.

The present invention will be described in more detail with reference to the following examples but is not to be construed to be limited thereto.

In the following examples, "%" for concentration denotes weight per volume percent unless otherwise specified.

EXAMPLE 1

Extraction of mRNA from IFO 6785 Strain of *Hypomyces mycophilus*

YM medium (50 ml) (containing 0.3% yeast extract (Kyokuto Seiyaku), 0.3% malt extract (Kyokuto Seiyaku), 0.5% polypeptone (Nihon Seiyaku), 2.0% glucose (Wako Pure Chemical); pH 6.0) was placed in a 500-ml baffled Erlenmeyer flask, autoclaved, and used as the growth medium for producing D-aminoacylase by *Hypomyces mycophilus* IFO 6785 strain. The fungal strain previously grown in YM agar medium (containing 0.3% yeast extract, 0.3% malt extract, 0.5% polypeptone, 2.0% glucose (Wako Pure Chemical), and 1.5% agar (Wako Pure Chemical); pH 6.0) on the plate was excised in about 5-ml piece using a sterilized surgical knife, inoculated into the above-described medium in the flask, and incubated on a rotary shaker at 145 rpm and 25° C. for 96 h.

Immediately after the culture completed, cells were harvested by suction filtration with a No. 5A filter paper (Toyo Roshi Co. Ltd.). The collected cells were transferred to a plastic bag and then frozen with liquid nitrogen. Messenger RNA was extracted and purified from the frozen cells by using a QuickPrep mRNA Purification Kit (Amersham Pharmacia Biotech) according to the protocol.

EXAMPLE 2

Preparation of cDNA Library

A cDNA library was prepared by the method of Gubler and Hoffman (Gene, 25:263–269, 1983). The first and second strands of cDNA were synthesized by using 3.0 μg mRNA, oligo(dT)$_{18}$ linker-primer (containing a NotI site) shown in SEQ ID NO: 2, 5-methyl dCTP, RAV-2 Reverse Transcriptase (TaKaRa Shuzo), and SuperScript II Reverse Transcriptase (GIBCO BRL). After the second strand was synthesized, both ends of the DNA were blunted with Klenow fragment and ligated with BamHI (BglII)-SmaI adaptor (TaKaRa Shuzo). The DNA was subjected to NotI digestion, and then treated with SUPREC-02 (TaKaRa Shuzo) for the removal of low-molecular-weight DNA to prepare cDNA inserts. The cDNA inserts were ligated into pAP3neo vector (linearized with BglII and NotI). The resulting plasmids dissolved in TE buffer was stored at −20° C. until it was used.

EXAMPLE 3

Screening of cDNA Library for the 5'-End and 3'-End Regions of the Target Gene

A pair of sense and antisense primers was synthesized based on each of the amino acid sequences of DAACFL35 and DAACFL42. Namely, four primers in total were synthesized. As will be described later, the amino acid sequences of DAACFL35 and DAACFL42 have been identified as partial amino acid sequences of D-aminoacylase purified from *Hypomyces mycophilus* IFO 6785 strain. The respective nucleotide sequences are shown in SEQ ID NO: 3 (35F1), SEQ ID NO: 4 (35F2), SEQ ID NO: 5 (42R1), and SEQ ID NO: 6 (42R2).

The first-round PCR was performed in 50 μl reaction mixture containing 100 pmol 35F1 primer, 100 pmol 42R1 primer, 10 pmol dNTP, 1 μl of the cDNA library prepared in Example 2, 2 U of ExTaq DNA polymerase (TaKaRa Shuzo), and ExTaq Buffer (TaKaRa Shuzo) with a thermal cycler, GeneAmp PCR System 9600 (Perkin Elmer) for 30 cycles of denaturation at 94° C. for 30 seconds, annealing at 55° C. for 60 seconds, and extension at 72° C. for 2 minutes.

Subsequently, the second-round PCR was carried out in 50 μl reaction mixture-containing 100 pmol 35F2 primer, 100 pmol 42R2 primer, 10 pmol dNTP, 0.1 μl of the first-round PCR solution, 2 U of ExTaq DNA polymerase (TaKaRa Shuzo), and ExTaq Buffer (TaKaRa Shuzo) with the same program as that used in the first round. A sample of the PCR solution was subjected to agarose gel electrophoresis, and a specific band was detected on the gel.

D-aminoacylase was isolated from *Hypomyces mycophilus* IFO 6785 strain and its amino acid sequence was determined partially as follows.

*Hypomyces mycophilus* IFO 6785 strain was cultured at 25° C., 200 rpm, 1 v.v.m., without pressure for 44 h in 20 liters of a liquid medium (containing 0.3% yeast extract (Kyokuto Seiyaku), 0.3% malt extract (Kyokuto Seiyaku), 1.0% polypeptone (Wako Pure Chemical), 2.0% glucose (Wako Pure Chemical), and 0.01% silicon FS028; pH 6.0) then placed in a 30-1 jar fermentor.

After culturing, the culture was immediately cooled in ice-water and filtered using No. 5A filter paper (Toyo Roshi) by suction to collect the fungal cells. The cells thus collected were washed with physiological saline solution, recovered again by the suction filtration, and stored at −90° C. till use.

Frozen cells (about 100 g) were wrapped in double-layered plastic bags with zippers and pulverized in an aluminum vat using a mallet. Pulverized cells were added to 50 mM Tris-HCl (pH 9.0) containing 1 μM leupeptin, 1 μM pepstatin A, 1 mM PMSF, and 0.01% 2-ME to prepare a cell suspension. The suspension was then subjected to continuous trituration with a Dyno mill type KDL (Wiley A. Bachofen, Based, Switzerland) using 0.2- to 0.5-mm glass beads.

The resulting cell triturate was centrifuged (with a Hitachi Koki centrifuge 20PR-52D using a RPR-9 rotor) at 8,000 rpm (6,000× g) at 4° C. for 30 min to sediment unbroken cells and cell debris. The supernatant thus obtained was assayed to determine the protein concentration. The total protein amounted to 61,500 mg. The 1/10th weight of protamine sulfate was then added dropwise to the supernatant as a 3% solution (in the same buffer used for the trituration) with stirring at low temperature, and the mixture was stirred for an additional 2 h. The resulting mixture was centrifuged (with a Hitachi Koki centrifuge 20PR-52D using an RPR-9 rotor) at 6,000 rpm (3,000× g) for 20 min at 4° C. to sediment microsomes and nucleic acids.

The supernatant was reversely dialyzed against 17 liters of 50 mM Tris-HCl (pH 9.0) containing 77% saturated ammonium sulfate, 0.1 mM PMSF, 0.1 μM leupeptin, 0.1 μM pepstatin A, and 0.01% 2-ME with stirring overnight. This procedure did not completely salt out D-aminoacylase, and ammonium sulfate in excess was added directly to the dialysate with stirring at low temperature. The precipitate was collected by centrifugation (with a Tomy Seiko RS-20BH centrifuge using a BH-9 rotor) at 10,000 rpm (16,000×g) at 4° C. for 20 min then suspended in a small amount of 10 mM Tris-HCl (pH 9.0) containing 0.1 mM PMSF, 0.1 μM leupeptin, 0.1 μM pepstatin A, and 0.01% 2-ME. The suspension was dialyzed against the same buffer (10 liter) for 4 h, and then against the same freshly replaced buffer (10 liter) overnight.

After dialyzed, the enzyme was further purified by anion exchange chromatography. Namely, the crude enzyme solution was adsorbed to an XK50 column (5.0 dia.×25 cm, 500 ml) packed with DEAE-Sepharose FF (both from Amersham Pharmacia Biotech) equilibrated with 10 mM Tris-HCl (pH 9.0) containing 0.01% 2-ME. After the column was washed with three volumes of the same buffer, the enzyme was eluted with a linear gradient of NaCl from 0 M to 0.5 M in seven volumes of the same buffer. The amount of protein in each fraction was estimated by measuring the absorbance at 280 nm.

D-Aminoacylase of the present invention was eluted with a buffer containing 0.20 to 0.25 M NaCl. Fractions containing the D-aminoacylase activity were combined, and concentrated fivefold using a UF membrane (Amicon, YM-10 76 mm dia.). Ammonium sulfate was added to the concentrate to 70% saturation, and the mixture was allowed to stand overnight to complete the precipitation. The mixture was then centrifuged (with a Hitachi Koki HIMAC CR26H centrifuge using a RR18A rotor) at 12,000 rpm (18,000× g) and 4° C. for 10 min to recover the precipitate. The recovered precipitate was suspended in 10 ml of 200 mM KPB (pH 8.5) containing 0.01% 2-ME and 0.3 M $Na_2SO_4$, and dialyzed against the same buffer (2 liters) overnight. Dialysis was performed then again against the same but freshly replaced buffer (2 liters) for 4 h.

The enzyme obtained by anion exchange chromatography was further purified by hydrophobic chromatography. Specifically, the enzyme was adsorbed to a Phenyl-Sepharose Hi-Load HP2.6/10 column (Amersham Pharmacia Biotech, 2.6 dia.×10 cm, 50 ml) equilibrated with 200 mM KPB (pH 8.5) containing 0.01% 2-ME and 0.3 M $Na_2SO_4$. After the column was washed with four volumes of the same buffer, the enzyme was eluted by linearly decreasing the concentration of $Na_2SO_4$ in the above-described buffer (buffer A) from 0.3 M to 0 M, that is, linearly increasing the concentration of 10 mM KPB (pH 8.5) containing 0.01% 2-ME from 0% to 100% in buffer A. The amount of protein in each fraction was estimated by measuring the absorbance at 280 nm. The D-aminoacylase activity was assayed in the same manner as described above.

Ammonium sulfate was added to the fractions containing the D-aminoacylase activity to 70% saturation, and the mixture was gently stirred for 2 h to form precipitates, which were recovered by centrifugation (with a Hitachi Koki HIMAC CR26H centrifuge using a RR18A rotor) at 12,000 rpm (18,000× g) and 4° C. for 10 min. The precipitate thus recovered was dissolved in about 3 ml of 10 mM Tris-HCl (pH 9.5) containing 0.01% 2-ME and 0.3 M NaCl.

The enzyme solution obtained by hydrophobic chromatography was further purified by gel filtration chromatography. Specifically, the enzyme was applied onto a Superdex 200 Hi-Load 1.6/60 column (Amersham Pharmacia Biotech, 1.6 dia.×60 cm, 120 ml) equilibrated with 10 mM Tris-HCl (pH 9.5) containing 0.01% 2-ME and 0.3 M NaCl, and eluted with the same buffer (240 ml) at a flow rate of 1 m/min. The amount of protein in each fraction was estimated by measuring the absorbance at 280 nm.

The fractions containing the D-aminoacylase activity were concentrated using a UF membrane (Amicon, YM-10, 43 mm dia.), diluted with 10 mM Tris-HCl (pH 9.5) containing 0.01% 2-ME, and concentrated again. The same procedure was repeated twice to desalt the sample.

The enzyme purified by gel filtration was further purified by anion exchange chromatography. Specifically, the enzyme was adsorbed to a MonoQ HR 5/5 column (Amersham Pharmacia Biotech, 0.5 dia.×5 cm, 1.0 ml) equilibrated with 10 mM Tris-HCl (pH 9.0) containing 0.01% 2-ME. After the column was washed with three volumes of the same buffer, the enzyme was eluted with a linear gradient of NaCl from 0 M to 0.6 M in 21 volumes of the same buffer. The amount of protein in each fraction was estimated by measuring the absorbance at 280 nm. The fractions containing proteins were pooled and considered to be the purified D-aminoacylase.

After a solution containing the purified enzyme (1 nmol) was concentrated by ultrafiltration to 50 μl, 50 mM Tris-HCl (pH 9.0) containing 8 M urea (150 μl) was added to the concentrated solution and the mixture was kept at 37° C. for 1 h. After 200 μl of 50 mM Tris-HCl (pH 9.0) was added, the mixture was digested with lysyl endopeptidase (5 pmol) at 30° C. overnight. Digested products were fractionated by high-performance liquid chromatography using an ODS column (column, TSK gel ODS-120T (4.6 dia.×250 mm) (Tosoh); eluent, buffer A (0.1% TFA) and buffer B (80% CH$_3$CN containing 0.095% TFA); detection, 214 nm; flow rate, 1.0 ml/min; programmed gradient elution), and fractions were collected.

The resulting fractions were concentrated by a centrifugal evaporator (UNISCIENCE, UNIVAP) and sequenced with a protein sequencer (A477, Applied Biosystems). Of the five partial amino acid sequences determined, two were DAACFL35 (GFILSPGFIDMHAHSDLYLLSHPTH/SEQ ID NO: 26) and
DAACFL42 (VLADEYPQAFYAPHAYSRGF/SEQ ID NO: 27).

EXAMPLE 4

Direct Sequencing of PCR Products

The DNA fragments obtained in Example 3 were extracted with phenol/chloroform, and then recovered by ethanol precipitation. After agarose gel electrophoresis, the band of interest was cut out, and the DNA was purified by using SUPREC-01 (TaKaRa Shuzo). The nucleotide sequence of the DNA was determined by direct sequencing using a BigDye Terminator Cycle Sequencing FS Ready Reaction Kit with an ABI 377 automatic sequencer (Applied Biosystems). Primers used were the same as those used for the PCR reaction. The determined nucleotide sequence was shown in SEQ ID NO: 7.

EXAMPLE 5

Screening of cDNA Library for the 3'-End Region of the Target Gene

A pair of primers, F56 (SEQ ID NO: 8) and F241 (SEQ ID NO: 9), were synthesized based on the sequence determined in Example 4. Primers, pAP3R1 (SEQ ID NO: 10) and T3 (SEQ ID NO: 11), were synthesized as vector primers. The screening was carried out by nested PCR using these primers.

The first-round PCR was performed in 50 μl reaction mixture containing 10 pmol pAP3R1 primer, 10 pmol F56 primer, 10 pmol dNTP, 1 μl of the cDNA library prepared in Example 2, 2 U of ExTaq DNA polymerase (TaKaRa Shuzo), and ExTaq Buffer (TaKaRa Shuzo) with a thermal cycler, Thermal Cycler SP (TaKaRa Shuzo) for 30 cycles of denaturation at 94° C. for 30 seconds, annealing at 55° C. for 30 seconds, and extension at 72° C. for 60 seconds.

Subsequently, the second-round PCR was carried out in 50 μl reaction mixture containing 10 pmol T3 primer, 10 pmol F241 primer, 10 pmol dNTP, 1 μl of the first-round PCR solution, 2 U of ExTaq DNA polymerase (TaKaRa Shuzo) and ExTaq Buffer (TaKaRa Shuzo) with the same program as that used in the first round. A sample of the PCR solution was subjected to agarose gel electrophoresis, and a specific band of about 1.3 kbp was detected on the gel.

The nucleotide sequence of the PCR products was determined by direct sequencing by using the primer walking method according to Example 4. The determined nucleotide sequence was shown in SEQ ID NO: 12. Primers used were F241, F3 (SEQ ID NO: 13), and F4 (SEQ ID NO: 14).

EXAMPLE 6

Screening of cDNA Library for the 5'-End Region of the Target Gene

Primers, R130 (SEQ ID NO: 15), R96 (SEQ ID NO: 16), and R47 (SEQ ID NO: 17) were synthesized based on the sequence determined in Example 4. Primers, pAP3F2 (SEQ ID NO: 18) and pAP3F1 (SEQ ID NO: 19), were synthesized as vector primers. The screening was carried out by nested PCR using these primers.

The first-round PCR was performed in 50 μl reaction mixture containing 10 pmol pAP3F2 primer, 10 pmol R130 primer, 10 pmol dNTP, 1 μl of the cDNA library prepared in Example 2, 2 U of ExTaq DNA polymerase (TaKaRa Shuzo), and ExTaq Buffer (TaKaRa Shuzo) with a thermal cycler, Thermal Cycler SP (TaKaRa Shuzo) for 30 cycles of denaturation at 94° C. for 30 seconds, annealing at 55° C. for 30 seconds, and extension at 72° C. for 60 seconds. Subsequently, the second-round PCR was carried out in 50 μl reaction mixture containing 10 pmol pAP3F1 primer, 10 pmol R96 primer, 10 pmol dNTP, 1 μl of the first-round PCR solution, 2 U of ExTaq DNA polymerase (TaKaRa Shuzo), and ExTaq Buffer (TaKaRa Shuzo) with the same program as that used in the first round. Further, the third-round PCR was carried out in 50 μl reaction mixture containing 10 pmol pAP3F1 primer, 10 pmol R47 primer, 10 pmol dNTP, 1 μl of the second-round PCR product, 2 U of ExTaq DNA polymerase (TaKaRa Shuzo), and ExTaq Buffer (TaKaRa Shuzo) with the same program as that used in the first round. A sample of the PCR solution was subjected to agarose gel electrophoresis, and a specific band of about 400 bp was detected on the gel.

The nucleotide sequence of the PCR products was determined by direct sequencing according to Example 4. The primer used was R47. The result showed that the amplified DNA was derived from the target gene and contained the translation initiation codon in its sequence. The determined sequence is shown in SEQ ID NO: 20.

EXAMPLE 7

PCR Screening of cDNA Library for the Target Gene

Primers, Acy5'-1 (SEQ ID NO: 21), Acy5'-2 (SEQ ID NO: 22), Acy3'-1 (SEQ ID NO: 23) and Acy3'-2 (SEQ ID NO: 24), were synthesized based on the determined nucleotide sequences corresponding to the 5' and 3' ends of the target gene obtained by PCR screening (conducted in Examples 5 and 6). The screening was carried out by nested PCR using these primers.

The first-round PCR was performed in 50 μl reaction mixture containing 10 pmol Acy5'-1 primer, 10 pmol Acy3'-1 primer, 10 pmol dNTP, 1 μl of the cDNA library prepared in Example 2, 2 U of Pyrobest DNA polymerase (TaKaRa Shuzo), and Pyrobest Buffer (TaKaRa Shuzo) with a thermal cycler, Thermal Cycler SP (TaKaRa Shuzo) for 30 cycles of denaturation at 94° C. for 30 seconds, annealing at 55° C. for 30 seconds, and extension at 72° C. for 90 seconds. Subsequently, the second-round PCR was carried out in 50 μl reaction mixture containing 10 pmol Acy5'-2 primer, 10 pmol Acy3'-2 primer, 10 pmol dNTP, 1 μl of the first-round PCR solution, 2 U of Pyrobest DNA polymerase (TaKaRa Shuzo), and Pyrobest Buffer (TaKaRa Shuzo) with the same program as that used in the first round.

A sample of the PCR solution was subjected to agarose gel electrophoresis, and a specific band was detected on the gel. The amplification products were purified according to Example 4. The fragments were digested with HindIII, and then subcloned in pUC 118 HindIII/BAP (TaKaRa Shuzo) and TaKaRa Ligation Kit ver.II (TaKaRa Shuzo). With the resulting plasmid, E. coli strain JM109 was transformed.

The transformants were grown on a plate of LB medium (1% bactotryptone, 0.5% bacto-yeast extract and 1% sodium chloride) containing ampicillin (50 μg/ml), 5-brome-4-chloro-3-indolyl-β-D-galactopyranoside (50 μg/ml), and isopropylthio-β-D-galacto-pyranoside (hereinafter referred to as IPTG).

Bacterial cells from a growing white colony on the plate was inoculated and cultured in a liquid LB medium. The plasmid was recovered from the cultured cells and the nucleotide sequence of the insert in the plasmid was determined by the single primer extension method. The determined sequence is shown in SEQ ID NO: 25. The 5'- and 3'-end sequences of the target cDNA were found in the nucleotide sequence determined, and the open reading frame (ORF) of the D-aminoacylase was searched and clarified in the nucleotide sequence. The DNA sequence determined is shown in SEQ ID NO: 1; the sequence of the protein encoded by the DNA is shown in SEQ ID NO: 2. The analysis and search of the sequences was performed by using computer software packages, GenetyxATSQ and Genetyx (both are products provided by Software Development Co., Ltd.).

EXAMPLE 8

Gene Expression in the Transformant

The transformants obtained in Example 7 were cultured with shaking in a liquid LB medium containing ampicillin (50 1g/ml) at 26° C. overnight, and then 0.1 mM IPTG was added to the culture. The shaking culture was prolonged at 30° C. for another 4 hours. After culturing, the bacterial cells were collected by centrifuge, washed with physiological saline to remove constituents of the medium. The cells were suspended in 50 mM Tris-HCl buffer (pH 7.5) containing 1% N-acetyl-D-tryptophan and 0.01% 2-mercaptoethanol to make a reaction mixture with total volume of I ml. Reaction was performed with shaking at 30° C. for 6 hours. E. coli JM109 strain was used as a control.

After the reaction was completed, bacterial cells were removed by centrifugation. The amount of amino acid produced in the resulting reaction supernatant was quantified by high performance liquid chromatography with an ODS column (column, Wakosil II 5C18 (4.6×250 mm) (Wako Pure Chemical Industries); eluate, $CH_3CN$/50 mM $KH_2PO_4$/$H_3PO_4$ (pH2.5, ratio=2:8); detection, absorbance at 280 nm; flow rate, 1.0 ml/min; column temperature, 40° C.). The retention time was 3.3 minutes for D-tryptophan or 8.5 minutes for N-acetyl-D-tryptophan.

The reaction supernatant of the transformant was found to contain 0.15 g/l D-tryptophan; such accumulation of D-tryptophan was not detected in the control supernatant.

What is claimed is:

1. A substantially purified polypeptide comprising SEQ ID NO:2.

2. A substantially purified polypeptide consisting of SEQ ID NO:2.

3. A substantially purified polypeptide encoded by a nucleic acid comprising SEQ ID NO:1.

* * * * *

SEQUENCE LISTING

```
<160> NUMBER OF SEQ ID NOS: 27

<210> SEQ ID NO 1
<211> LENGTH: 1677
<212> TYPE: DNA
<213> ORGANISM: Hypomyces mycophilus

<400> SEQUENCE: 1
atgcggactg aaattctctt ccactcagcc actgttatca ccggcgatga agcagcccag      60
ccctttgtgg ccgatgtgct ggtttcgaag ggactgattg ccaagattgg taacccggt      120 tccatcaatg caactccaga tacgcggcat ctcgacgtca caggctacat tctatctcct    180
ggtttcatcg atatgcatgc gcattcagac ctctacctac tctctcatcc tgaccacgag    240
gccaaaatca cccaaggatg cacaacgaaa gttgtgggcc aagacgggat atcatatgca    300
ccaattcgta atgtagacca gttgagggcg atccgagaac agattgctgg atggaatggc    360
aatcctacag atgaggagtg ccggacaact ctcaaaggcg ttggcatgtt tgaatggcag    420
actattgggg aatacttgga ttgtttggag agaaacagga cggccactaa tgtcgccatg    480
ttggttccgc aaggcaacct gagattattg gcatgtggcc catacgatac tccagcatct    540
gcagaagaga ttcaagatca aatccagctc ttgcgagagg ctatggctca gggtgctgtc    600
gggatgtcta gtggtctcac ttatacaccc ggcatgtatg cttccacgtc ggaactagct    660
tctctgtgcg cggccctcgc acaagaattt ccaggtgcat tctatgcgcc acatcataga    720
```

-continued

| | |
|---|---|
| agttatgggt tccaggccat cgaaagttat gccgaaatgt tggatctcgg agagtcaaca | 780 |
| ggctgtccca ttcatcttac acatgcaacg ctcaacttttt cagaaaataa gggtaaagct | 840 |
| cctgtcctca tctctatggt tgataaatct cttgctgcag gcgtggatgt cacacttgat | 900 |
| acgtatccat acttgccagg ctgtacaact ctggctgcat tgttgccaag ttgggcatct | 960 |
| gctggcggcc cacaagagac gcttaaaagg cttgaggatg cagaatcgag agaaaagatt | 1020 |
| cgtatagccg tggaaatcaa agggtgtgat ggcggccatg gtattccaac caactgggac | 1080 |
| gaaatccaga tcgggacgac taatgaacca tcaatcgcat cgtattctgg tcgcaggcta | 1140 |
| tcagaagtgg cacagtctgt tggaaagccg accatcgaag tcttttttcga gattctgcaa | 1200 |
| aaggataagc tcgcaacgag ctgtatcatg catgttggca atgaagaaaa cgtccgacag | 1260 |
| atcatgcagc atcgggtcca tatggcaggc agtgatggga tcttgcacgg gcagacgcta | 1320 |
| cacccacgag cttatggcac attcacgcgg tatttaggac actattctcg tgaactctcg | 1380 |
| cttgttgctc tgccgtccat gatcgctcac cttacatcac ggcccgccaa acgactttcg | 1440 |
| gtatatccat atcgcggtct gattgctgaa ggatccgctg ccgacattgt ggttttttaac | 1500 |
| cccgaaacgg taaaggatat gtcgacgtat aagagccaa aggtgccaag tcggggcatt | 1560 |
| agatttgttc tagttaacgg ccagatagct gtggacgaag caagatgac aggcacaaga | 1620 |
| gggggtaaaa cactgagaag aagcaccgat ggcaaggtga aggcaagaga tgagtaa | 1677 |

<210> SEQ ID NO 2
<211> LENGTH: 558
<212> TYPE: PRT
<213> ORGANISM: Hypomyces mycophilus

<400> SEQUENCE: 2

Met Arg Thr Glu Ile Leu Phe His Ser Ala Thr Val Ile Thr Gly Asp
 1               5                  10                  15

Glu Ala Ala Gln Pro Phe Val Ala Asp Val Leu Val Ser Lys Gly Leu
             20                  25                  30

Ile Ala Lys Ile Gly Asn Pro Gly Ser Ile Asn Ala Thr Pro Asp Thr
         35                  40                  45

Arg His Leu Asp Val Thr Gly Tyr Ile Leu Ser Pro Gly Phe Ile Asp
     50                  55                  60

Met His Ala His Ser Asp Leu Tyr Leu Leu Ser His Pro Asp His Glu
 65                  70                  75                  80

Ala Lys Ile Thr Gln Gly Cys Thr Thr Glu Val Val Gly Gln Asp Gly
                 85                  90                  95

Ile Ser Tyr Ala Pro Ile Arg Asn Val Asp Gln Leu Arg Ala Ile Arg
            100                 105                 110

Glu Gln Ile Ala Gly Trp Asn Gly Asn Pro Thr Asp Glu Glu Cys Arg
        115                 120                 125

Thr Thr Leu Lys Gly Val Gly Met Phe Glu Trp Gln Thr Ile Gly Glu
    130                 135                 140

Tyr Leu Asp Cys Leu Glu Arg Asn Arg Thr Ala Thr Asn Val Ala Met
145                 150                 155                 160

Leu Val Pro Gln Gly Asn Leu Arg Leu Leu Ala Cys Gly Pro Tyr Asp
                165                 170                 175

Thr Pro Ala Ser Ala Glu Glu Ile Gln Asp Gln Ile Gln Leu Leu Arg
            180                 185                 190

Glu Ala Met Ala Gln Gly Ala Val Gly Met Ser Ser Gly Leu Thr Tyr
        195                 200                 205

```
Thr Pro Gly Met Tyr Ala Ser Thr Ser Glu Leu Ala Ser Leu Cys Ala
    210                 215                 220

Ala Leu Ala Gln Glu Phe Pro Gly Ala Phe Tyr Ala Pro His His Arg
225                 230                 235                 240

Ser Tyr Gly Phe Gln Ala Ile Glu Ser Tyr Ala Glu Met Leu Asp Leu
                245                 250                 255

Gly Glu Ser Thr Gly Cys Pro Ile His Leu Thr His Ala Thr Leu Asn
            260                 265                 270

Phe Ser Glu Asn Lys Gly Lys Ala Pro Val Leu Ile Ser Met Val Asp
        275                 280                 285

Lys Ser Leu Ala Ala Gly Val Asp Val Thr Leu Asp Thr Tyr Pro Tyr
    290                 295                 300

Leu Pro Gly Cys Thr Thr Leu Ala Ala Leu Leu Pro Ser Trp Ala Ser
305                 310                 315                 320

Ala Gly Gly Pro Gln Glu Thr Leu Lys Arg Leu Glu Asp Ala Glu Ser
                325                 330                 335

Arg Glu Lys Ile Arg Ile Ala Val Glu Ile Lys Gly Cys Asp Gly Gly
            340                 345                 350

His Gly Ile Pro Thr Asn Trp Asp Glu Ile Gln Ile Gly Thr Thr Asn
        355                 360                 365

Glu Pro Ser Ile Ala Ser Tyr Ser Gly Arg Arg Leu Ser Glu Val Ala
    370                 375                 380

Gln Ser Val Gly Lys Pro Thr Ile Glu Val Phe Phe Glu Ile Leu Gln
385                 390                 395                 400

Lys Asp Lys Leu Ala Thr Ser Cys Ile Met His Val Gly Asn Glu Glu
                405                 410                 415

Asn Val Arg Gln Ile Met Gln His Arg Val His Met Ala Gly Ser Asp
            420                 425                 430

Gly Ile Leu His Gly Gln Thr Leu His Pro Arg Ala Tyr Gly Thr Phe
        435                 440                 445

Thr Arg Tyr Leu Gly His Tyr Ser Arg Glu Leu Ser Leu Val Ala Leu
    450                 455                 460

Pro Ser Met Ile Ala His Leu Thr Ser Arg Pro Ala Lys Arg Leu Ser
465                 470                 475                 480

Val Tyr Pro Tyr Arg Gly Leu Ile Ala Glu Gly Ser Ala Ala Asp Ile
                485                 490                 495

Val Val Phe Asn Pro Glu Thr Val Lys Asp Met Ser Thr Tyr Glu Glu
            500                 505                 510

Pro Lys Val Pro Ser Arg Gly Ile Arg Phe Val Leu Val Asn Gly Gln
        515                 520                 525

Ile Ala Val Asp Glu Gly Lys Met Thr Gly Thr Arg Gly Gly Lys Thr
    530                 535                 540

Leu Arg Arg Ser Thr Asp Gly Lys Val Lys Ala Arg Asp Glu
545                 550                 555
```

<210> SEQ ID NO 3
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 3
cccggcttca tcgacatgca     20

```
<210> SEQ ID NO 4
<211> LENGTH: 20
<212> TYPE: DNA
<213> ORGANISM: Artificial Sequence
<220> FEATURE:
<223> OTHER INFORMATION: Artificially Synthesized Primer Sequence
<220> FEATURE:
<221> NAME/KEY: misc_feature
<222> LOCATION: 18
<223> OTHER INFORMATION: n = A,T,C or G

<400> SEQUENCE: 4
ttcatcgaca tgcaygcnca                                                 20

<210> SEQ ID NO 5
<211> LENGTH: 20
<212> TYPE: DNA
<213> ORGANISM: Artificial Sequence
<220> FEATURE:
<223> OTHER INFORMATION: Artificially Synthesized Primer Sequence
<220> FEATURE:
<221> NAME/KEY: misc_feature
<222> LOCATION: 3, 6, 15
<223> OTHER INFORMATION: n = A,T,C or G

<400> SEQUENCE: 5
tgnggngcrt craangcytg                                                 20

<210> SEQ ID NO 6
<211> LENGTH: 20
<212> TYPE: DNA
<213> ORGANISM: Artificial Sequence
<220> FEATURE:
<223> OTHER INFORMATION: Artificially Synthesized Primer Sequence
<220> FEATURE:
<221> NAME/KEY: misc_feature
<222> LOCATION: 3, 9
<223> OTHER INFORMATION: n = A,T,C or G

<400> SEQUENCE: 6
aangcytgng grtaytcrtc                                                 20

<210> SEQ ID NO 7
<211> LENGTH: 321
<212> TYPE: DNA
<213> ORGANISM: Hypomyces mycophilus

<400> SEQUENCE: 7
ttcatcgaca tgcatgcgca gctggatggt caaccttgac aactacaaca agatactctc     60
tgtagacaaa aaatcggggg tcgtggtcat gcagagcggc attcgactat acacccttttg  120 cgaagagctg gagctacatg gcctggcaat gccgaacctg ggcagtataa acgagcaatc   180
catcgccggc gccatatcta caggcacaca cggcagcagc atccaccacg gcctcatgtc   240
tgaggatatt ctcgctctga aaatcactct cgcgggcggc aagacggagg catgctccaa   300
agacgaatac ccccaagcct t                                              321

<210> SEQ ID NO 8
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 8
aggccaaaat cacccaagga                                                 20
```

<210> SEQ ID NO 9
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 9
attggggaat acttggattg                                              20

<210> SEQ ID NO 10
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 10
ctggttcttt ccgcctcaga                                              20

<210> SEQ ID NO 11
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 11
attaaccctc actaaagggc                                              20

<210> SEQ ID NO 12
<211> LENGTH: 1325
<212> TYPE: DNA
<213> ORGANISM: Hypomyces mycophilus

<400> SEQUENCE: 12
caggacggcc actaatgtcg ccatgttggt tccgcaaggc aacctgagat tattggcatg    60
tggcccatac gatactccag catctgcaga agagattcaa gatcaaatcc agctcttgcg   120
agaggctatg gctcagggtg ctgtcgggat gtctagtggt ctcacttata cacccggcat   180
gtatgcttcc acgtcggaac tagcttctct gtgcgcggcc ctcgcacaag aatttccagg   240
tgcattctat gcgccacatc atagaagtta tgggttccag gccatcgaaa gttatgccga   300
aatgttggat ctcggagagt caacaggctg tcccattcat cttacacatg caacgctcaa   360
cttttcagaa aataagggta agctcctgt cctcatctct atggttgata aatctcttgc    420
tgcaggcgtg gatgtcacac ttgatacgta tccatacttg ccaggctgta caactctggc   480
tgcattgctg ccaagtcggg catctgctgg cggcccacaa gagacgctta aaaggcttga   540
ggatgcagaa tcgagagaaa agattcgtat agccgtggaa atcaaagggt gtgatggcgg   600
ccatggtatt ccaaccaact gggacgaaat ccagatcggg acgactaatg aaccatcaat   660
cgcatcgtat tctggtcgca ggctatcaga agtggcacag tctgttggaa agccgaccat   720
cgaagtcttt ttcgagattc tgcaaaagga taagctcgca acgagctgta tcatgcatgt   780
tggcaatgaa gaaaacgtcc gacagatcat gcagcatcgg gtccatatgg caggcagtga   840
tgggatcttg cacgggcaga cgctacaccc acgagcttat ggcacattca cgcggtattt   900
aggacactat tctcgtgaac tctcgcttgt tgctctgccg tccatgatcg ctcaccttac   960
atcacggccc gccaaacgac tttcggtata tccatatcgc ggtctgattg ctgaaggatc  1020
cgctgccgac attgtggttt ttaaccccga aacggtaaag gatatgtcga cgtatgaaga  1080

```
gccaaaggtg ccaagtcggg gcattagatt tgttctagtt aacggccaga tagctgtgga    1140
cgaaggcaag atgacaggca caagaggggg taaaacactg agaagaagca ccgatggcaa    1200
ggtgaaggca agagatgagt aaagtctcga tctgcatccg cgtgcccaac aacaggatca    1260
agtcgtcaca gcatgatacg gcaggctttg gagtagatac catgtcatgg gggaaatggt    1320
caata                                                                1325

<210> SEQ ID NO 13
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 13
cggagagtca acaggctgtc c                                              21

<210> SEQ ID NO 14
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 14
cgcaggctat cagaagtggc                                                20

<210> SEQ ID NO 15
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 15
atcgccctca actggtctac                                                20

<210> SEQ ID NO 16
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 16
catatgatat cccgtcttgg                                                20

<210> SEQ ID NO 17
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 17
gattttggcc tcgtggtcag                                                20

<210> SEQ ID NO 18
<211> LENGTH: 22
<212> TYPE: DNA
<213> ORGANISM: Artificial Sequence
<220> FEATURE:
<223> OTHER INFORMATION: Artificially Synthesized Primer Sequence
```

```
<400> SEQUENCE: 18
cctcagtgga tgttgccttt ac                                              22

<210> SEQ ID NO 19
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 19
gcctgtacgg aagtgttact                                                 20

<210> SEQ ID NO 20
<211> LENGTH: 253
<212> TYPE: DNA
<213> ORGANISM: Hypomyces mycophilus

<400> SEQUENCE: 20
gtgagagagt aggtagaggt ctgaatgcgc atgcatatcg atgaaaccag gagatagaat     60
gtagcctgtg acgtcgagat gccgcgtatc tggagttgca ttgatggaac cggggttacc    120
aatcttggca atcagtccct tcgaaaccag cacatcggcc acaaagggct gggctgcttc    180
atcgccggtg ataacagtgg ctgagtggaa gagaatttca gtccgcatcg ttggcaatgg    240
gaattcttct ggt                                                      253

<210> SEQ ID NO 21
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 21
gagaagctta cagaattctc tccattattg ac                                   32

<210> SEQ ID NO 22
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 22
gagaagctta ccagaagaat tcccattgcc                                      30

<210> SEQ ID NO 23
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 23
gagaagcttg tacgatgaat aaatatatgt gt                                   32

<210> SEQ ID NO 24
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 24
```

-continued

```
gagaagctta ttgaccattt cccccatgac                                  30
```

<210> SEQ ID NO 25
<211> LENGTH: 1897
<212> TYPE: DNA
<213> ORGANISM: Hypomyces mycophilus

<400> SEQUENCE: 25

```
agcttgacca tgattacgaa ttcgagctcg gtacccgggg atcctctaga gtcgacctgc    60
aggcatgcaa gcttaccaga agaattccca ttgccaacga tgcggactga aattctcttc   120
cactcagcca ctgttatcac cggcgatgaa gcagcccagc cctttgtggc cgatgtgctg   180
gtttcgaagg gactgattgc caagattggt aaccccggtt ccatcaatgc aactccagat   240
acgcggcatc tcgacgtcac aggctacatt ctatctcctg gtttcatcga tatgcatgcg   300
cattcagacc tctacctact ctctcatcct gaccacgagg ccaaaatcac caaggatgc    360
acaacggaag ttgtgggcca agacgggata tcatatgcac caattcgtaa tgtagaccag   420
ttgagggcga tccgagaaca gattgctgga tggaatggca atcctacaga tgaggagtgc   480
cggacaactc tcaaaggcgt tggcatgttt gaatggcaga ctattgggga atacttggat   540
tgtttggaga gaaacaggac ggccactaat gtcgccatgt tggttccgca aggcaacctg   600
agattattgg catgtggccc atacgatact ccagcatctg cagaagagat tcaagatcaa   660
atccagctct tgcgagaggc tatggctcag ggtgctgtcg ggatgtctag tggtctcact   720
tatacacccg gcatgtatgc ttccacgtcg gaactagctt ctctgtgcgc ggccctcgca   780
caagaatttc caggtgcatt ctatgcgcca catcatagaa gttatgggtt ccaggccatc   840
gaaagttatg ccgaaatgtt ggatctcgga gagtcaacag gctgtcccat tcatcttaca   900
catgcaacgc tcaactttc agaaaataag ggtaaagctc ctgtcctcat ctctatggtt   960
gataaatctc ttgctgcagg cgtggatgtc acacttgata cgtatccata cttgccaggc  1020
tgtacaactc tggctgcatt gttgccaagt tgggcatctg ctggcggccc acaagagacg  1080
cttaaaaggc ttgaggatgc agaatcgaga gaaaagattc gtatagccgt ggaaatcaaa  1140
gggtgtgatg gcggccatgg tattccaacc aactgggacg aaatccagat cgggacgact  1200
aatgaaccat caatcgcatc gtattctggt cgcaggctat cagaagtggc acagtctgtt  1260
ggaaagccga ccatcgaagt ctttttcgag attctgcaaa aggataagct cgcaacgagc  1320
tgtatcatgc atgttggcaa tgaagaaaac gtccgacaga tcatgcagca tcgggtccat  1380
atggcaggca gtgatgggat cttgcacggg cagacgctac acccacgagc ttatggcaca  1440
ttcacgcggt atttaggaca ctattctcgt gaactctcgc ttgttgctct gccgtccatg  1500
atcgctcacc ttacatcacg gcccgccaaa cgactttcgg tatatccata tcgcggtctg  1560
attgctgaag gatccgctgc cgacattgtg gttttttaacc ccgaaacggt aaaggatatg  1620
tcgacgtatg aagagccaaa ggtgccaagt cggggcatta gatttgttct agttaacggc  1680
cagatagctg tggacgaagg caagatgaca ggcacaagag ggggtaaaac actgagaaga  1740
agcaccgatg gcaaggtgaa ggcaagagat gagtaaagtc tcgatctgca tccgcgtgcc  1800
caacaacagg atcaagtcgt cacagcatga tacggcaggc tttggagtag ataccatgtc  1860
atgggggaaa tggtcaataa gcttggcact ggccgtc                           1897
```

<210> SEQ ID NO 26
<211> LENGTH: 25
<212> TYPE: PRT

```
<213> ORGANISM: Hypomyces mycophilus

<400> SEQUENCE: 26

Gly Phe Ile Leu Ser Pro Gly Phe Ile Asp Met His Ala His Ser Asp
 1               5                  10                  15

Leu Tyr Leu Leu Ser His Pro Thr His
            20                  25

<210> SEQ ID NO 27
<211> LENGTH: 20
<212> TYPE: PRT
<213> ORGANISM: Hypomyces mycophilus

<400> SEQUENCE: 27

Val Leu Ala Asp Glu Tyr Pro Gln Ala Phe Tyr Ala Pro His Ala Tyr
 1               5                  10                  15

Ser Arg Gly Phe
            20
```